United States Patent [19]

Wilkes et al.

[11] Patent Number: 4,900,867
[45] Date of Patent: Feb. 13, 1990

[54] PROCESS FOR PRODUCING FLUOROSULFONAMIDES

[75] Inventors: Bernd Wilkes, Hanover; Dieter Naumann, Dortmund; Werner Rudolph, Hanover; Ruediger Sander, Sehnde, all of Fed. Rep. of Germany

[73] Assignee: Kali-Chemie Aktiengesellschaft, Hanover, Fed. Rep. of Germany

[21] Appl. No.: 69,094

[22] Filed: Jul. 2, 1987

[30] Foreign Application Priority Data

Jul. 10, 1986 [DE] Fed. Rep. of Germany ....... 3623184

[51] Int. Cl.$^4$ .................. C07C 143/78; C07C 143/74
[52] U.S. Cl. ........................................ 564/91; 564/96; 564/98
[58] Field of Search ............................. 564/91, 96, 98

[56] References Cited

U.S. PATENT DOCUMENTS

| | | | |
|---|---|---|---|
| 1,955,207 | 4/1934 | Stotter et al. | 564/91 |
| 2,590,390 | 3/1952 | Earland | 564/91 |
| 3,917,688 | 11/1975 | Barton et al. | |
| 4,479,901 | 10/1984 | Barnette. | |
| 4,697,011 | 9/1987 | DesMarteau. | |

FOREIGN PATENT DOCUMENTS 0211578  2/1987  European Pat. Off..
1369957 10/1974 United Kingdom.

OTHER PUBLICATIONS

Barnette, *J. Amer. Chem. Soc.*, 106:452–454 (1984).
Lee et al., *J. Amer. Chem. Soc.*, 108:2445–2447 (1986).
Kalichemie brochure entitled "N-Fluorosulfonamides (NFS), Electrophilic Fluorinating Reagents", May 1987.
*Chemical Abstracts*, 80:108209r (1974).
Grakauskas et al., *J. Org. Chem.*, 34:2840–2845 (1969).
Grakauskas et al., *J. Org. Chem.*, 35:1545–1549 (1969).
Barton et al., *J.C.S. Perkin I*, pp. 732–738 (1974).
Seguin et al., *J. Fluorine Chem.*, 15:201–211 (1980).
Singh, *J. Amer. Chem. Soc.*, 109:7194–7196 (1987).

*Primary Examiner*—Alan Siegel
*Attorney, Agent, or Firm*—Foley & Lardner, Schwartz, Jeffery, Schwaab, Mack, Blumenthal & Evans

[57] ABSTRACT

A process for producing N-fluorosulfonamides by reaction of a sulfonamide with fluorine in a solvent mixture of halogenated hydrocarbon an nitrile is described together with new N-fluorosulfonamides which are produced in accordance with this process.

16 Claims, No Drawings

PROCESS FOR PRODUCING FLUOROSULFONAMIDES

BACKGROUND OF THE INVENTION

The present invention relates to a process for producing N-fluorosulfonamides as well as to new N-fluorosulfonamides which can be produced according to this process.

The production of N-fluorosulfonamides from sulfonamides by reaction with fluorination agents in a solvent is known. These processes, however, are uneconomical, on the one hand, due to the utilization of expensive fluorinating agents such as, for example, hypofluorites, or on the other hand, when fluorine is utilized as the fluorinating agent, one must work at very low temperatures with strongly diluted fluorine because of the lack of selectivity of the reaction of fluorine, and even then the yields of fluorosulfonamides are not satisfactory. Thus, for example, the production of N-fluoro-N-alkylsulfonamides is reported in *Journal of the American Chemical Society*, 1984, pages 452 et seq. There the reaction is undertaken with 1 to 5 percent fluorine in nitrogen at −78° C. in $CFCl_3/CHCl_3$ as a solvent, and yields in the range from 11 to 71 percent are thereby achieved.

SUMMARY OF THE INVENTION

It is the object of the invention to overcome the disadvantages of known processes and to make available a new, improved process for producing N-fluorosulfonamides.

It is a further object of the invention to provide new N-fluorosulfonamides which can be produced according to the process of the invention.

The objects of the invention are achieved according to a first aspect of the invention by providing a process for producing N-fluorosulfonamides comprising reacting a sulfonamide corresponding to the Formula (I):

$$R^1-SO_2-NH-R^2 \qquad (I)$$

in which
$R^1$ represents alkyl with 1 to 10 C-atoms or alkyl with 1 to 10 C-atoms substituted by at least 1 F-atom, or aryl or aryl substituted by 1 to 5 substituents independently selected from the group consisting of F-atoms, $CF_3$-groups, and $CH_3$-groups, with the proviso that not more than 2 substituents may be $CF_3$-groups or $CH_3$-groups, and
$R^2$ represents alkyl containing 1 to 6 C-atoms,
with elemental fluorine in a solvent mixture comprising a halogenated hydrocarbon and a nitrile, and recovering the resulting N-fluorosulfonamide from the reaction mixture.

According to a further aspect of the invention, the objects are achieved by providing an N-fluorosulfonamide corresponding to the Formula (II)

$$R^3-SO_2-NF-R^2 \qquad (II)$$

in which
$R^3$ represents a group containing at least one F-atom selected from the group consisting of phenyl, tolyl, or alkyl with 1 to 10 carbon atoms, and
$R^2$ represents an alkyl group containing 1 to 6 C-atoms.

DETAILED DESCRIPTION OF PREFERRED EMBODIMENTS

The process of the invention for producing N-fluorosulfonamides starts from the general process in which sulfonamides are reacted with a fluorination agent in a solvent, and the process of the invention is characterized in that a sulfonamide corresponding to the Formula (I)

$$R^1-SO_2-NH-R^2 \qquad (I)$$

in which
$R^1$ represents alkyl with 1 to 10 C-atoms, preferably 1 to 8 C-atoms, optionally substituted by one or more F-atoms, or aryl, such as phenyl or naphthyl, optionally substituted by 1 to 5 F-atoms and/or 1 to 2 $CF_3$- or $CH_3$- groups, and
$R^2$ represents alkyl with 1 to 6 C-atoms,
is reacted with elemental fluorine in a solvent mixture of a halogenated hydrocarbon and a nitrile, and the resulting N-fluorosulfonamide is isolated from the reaction mixture.

Preferred alkyl substituents $R^1$ include perfluoroalkyl substituents such as, for example, perfluoroctyl, pentafluoroethyl, and trifluoromethyl, particularly trifluoromethyl. Preferred aryl substituents $R^1$ include tolyl, trifluoromethylphenyl, fluorophenyl, and perfluorophenyl.

Possible $R^2$ substituents include straight or branched alkyl groups. Suitable unbranched alkyl groups include, in particular, methyl, ethyl, propyl, butyl, pentyl, and hexyl. Suitable branched alkyl groups may be iso-propyl, iso-butyl, sec.-butyl, tert.-butyl, 1-, 2-, or 3-methylbutyl, 2- or 3-ethylpropyl, or 1,1-, 2,2-, or 3,3-dimethylpropyl. Particularly preferred branched alkyl groups are iso-propyl, iso-butyl, sec.-butyl, and neo-pentyl (2,2-dimethylpropyl). Especially preferred branched alkyl groups are those in which branching does not occur at the carbon atom bonded to the nitrogen. Such branched alkyl groups include, for example, iso-butyl, sec.-butyl, and neo-pentyl.

Preferably a halogenated hydrocarbon selected from the group consisting of chlorinated hydrocarbons and/or fluorochlorohydrocarbons having 1 to 3 carbon atoms is selected as a component of the solvent mixture. Dichloromethane, chloroform, carbon tetrachloride, fluorotrichloromethane, trifluorotrichloroethane, and tetrafluorodichloroethane have proved to be particularly suitable halogenated hydrocarbons. With halogenated hydrocarbons having 2 or 3 carbon atoms which form isomers, all of the known isomers can be utilized. Generally, the asymmetrically substituted isomers are preferred. Thus, for example, besides 1,1,1-trifluorotrichloroethane, 1,1,2-trifluorotrichloroethane is preferred as a trifluorotrichloroethane solvent component.

As a further essential component of the solvent mixture, a nitrile is utilized, whereby acetonitrile and/or propionitrile are preferred, particularly acetonitrile.

The mixing ratio between the halogenated hydrocarbon and the nitrile can be varied throughout a very wide range. Volume mixing proportions of halogenated hydrocarbon to nitrile in the range from 10:1 to 1:10, preferably 2:1 to 1:2, have proved satisfactory.

The fluorinating agent fluorine is preferably utilized in admixture with inert gases such as nitrogen, sulfurhexafluoride ($SF_6$), carbontetrafluoride ($CF_4$) or noble gases such as helium, neon, argon, or krypton. The preferred inert gas is nitrogen. Mixtures of fluorine and inert gas which contain up to 30 volume percent fluorine can be utilized for the fluorination. Very good results have been obtained with from 10 to 25 volume percent fluorine.

The temperature at which the reaction is carried out can be varied throughout a wide range and lies particularly in the range from +10° to −80° C. The selection of the temperature depends in each individual case on the selection of the reaction conditions such as fluorine concentration, composition of the solvent mixture, etc.

A further embodiment of the invention envisions bringing the reaction mixture into contact with an adsorption agent for hydrogen fluoride during and/or after the reaction and removing the hydrogen fluoride formed during the course of the reaction in this manner. All known adsorption agents for hydrogen fluoride which do not interfere with the reaction, i.e., which do not react with the N-fluorosulfonamide which is formed, may be used as adsorption means. Alkali fluorides, alkali hydrogencarbonates, and alkali carbonates, particularly sodium fluoride, have proved especially suitable as adsorption agents.

The work-up of the reaction mixture can be accomplished in a generally known manner by chromatographic methods, for example, column chromatography. It is, however, also possible to work up the reaction mixture by distillation. This possibility is primarily usable successfully when the hydrogen fluoride has been carefully removed from the mixture which results from the reaction.

In one particular variation, the invention contemplates carrying out the process continuously by (a) continuously introducing in controlled fashion a solution of a sulfonamide corresponding to Formula (I) in a solvent mixture of halogenated hydrocarbon and nitrile together with gaseous fluorine into a reactor equipped with a thermostat, (b) circulating the reaction mixture in a circuit through an adsorption agent for hydrogen fluoride, (c) continuously withdrawing reaction mixture from the reactor and/or from the circuit of step (b) in accordance with the introduction of reaction components, (d) if necessary, removing from the withdrawn reaction mixture by means of an adsorption agent any hydrogen fluoride which is still present, and (e) recovering the N-fluorosulfonamide, preferably by means of a chromatographic process or by distillation.

The process of the invention is distinguished in comparison to known processes by significant advantages. Thus, it is possible to obtain the reaction product in greatly improved yields. Further, practically no side products can be detected, i.e., in the process of the invention, the reaction proceeds with very high selectivity.

A part of the compounds produced according to the process of the invention are new. In particular, these are N-fluorosulfonamides corresponding to the Formula (II)

in which $R^3$ represents a residue containing 1 or more F-atoms selected from the group consisting of phenyl, tolyl or alkyl having 1 to 10 carbon atoms, preferably 1 to 8 carbon atoms, and $R^2$ represents an alkyl residue with 1 to 6 carbon atoms.

Specific examples of these new compounds include, in particular, those compounds of Formula (II) in which the substituents $R^3$ and $R^2$ have the meanings listed in the following Table 1:

TABLE 1

| $R^3$ | Compounds of Formula (II) $R^2$ |
|---|---|
| $CF_3$ | $CH_3$, $C_2H_5$, n-$C_3H_7$, n-$C_4H_9$, sec-$C_4H_9$ iso-$C_4H_9$, n-$C_5H_{11}$, neo-$C_5H_{11}$, n-$C_6H_{13}$ |
| $C_2F_5$ | $CH_3$, $C_2H_5$, n-$C_3H_7$, n-$C_4H_9$, sec-$C_4H_9$ iso-$C_4H_9$, n-$C_5H_{11}$, neo-$C_5H_{11}$, n-$C_6H_{13}$ |
| $C_8F_{17}$ | $CH_3$, $C_2H_5$, n-$C_3H_7$, n-$C_4H_9$, sec-$C_4H_9$ iso-$C_4H_9$, n-$C_5H_{11}$, neo-$C_5H_{11}$, n-$C_6H_{13}$ |
| $C_6H_4F$ (para F) | $C_2H_5$, n-$C_3H_7$, n-$C_4H_9$, sec-$C_4H_9$ iso-$C_4H_9$, n-$C_5H_{11}$, neo-$C_5H_{11}$, n-$C_6H_{13}$ |
| $C_6H_4CF_3$ (para $CF_3$) | $CH_3$, $C_2H_5$, n-$C_3H_7$, n-$C_4H_9$, sec-$C_4H_9$ iso-$C_4H_9$, n-$C_5H_{11}$, neo-$C_5H_{11}$, n-$C_6H_{13}$ |
| $C_6F_5$ | $CH_3$, $C_3H_5$, n-$C_3H_7$, n-$C_4H_9$, sec-$C_4H_9$ iso-$C_4H_9$, n-$C_5H_{11}$, neo-$C_5H_{11}$, n-$C_6H_{13}$ |

The following Examples illustrate the invention in further detail without limiting its scope. Examples 1 and 3 are examples of the invention. Example 2 is a comparative example.

EXAMPLE 1

Fifty g (207 mmol) p-toluene-N-neo-pentylsulfonamide were dissolved in 300 ml of a mixture of $CH_3CN$ and $CCl_3F$ in a ratio (by volume) of 1:1 and cooled to −30° C. in a temperature-controlled reactor. For better mixing, the reaction solution was circulated by means of a hydrogen fluoride (HF) and fluroine ($F_2$) resistant pump. The fluorine/nitrogen gas mixture (15 volume percent $F_2$, 85 percent $N_2$) was then introduced into the solution. After reaching a degree of conversion of approximately 95 percent (determined by thin layer chromatography), the flow of fluorine was interrupted and the solution was washed free of fluorine. To remove the hydrogen fluoride, the reaction solution was filtered over NaF pellets. Further work-up was achieved by removing the solvent in a vacuum and purifying the oily raw product by column chromatography ($SiO_2$, $CH_2Cl_2$). Unreacted starting material was recycled.
Yield: 36.5 g=approx. 76 percent
Selectivity: 98–99 percent
Purity: >97 percent Surprisingly, the product, which melts at 58° C., can be distilled under high vacuum without decomposing.
Boiling Point: 135° C./3×10$^{-3}$ torr
$\delta^{19}$F-NMR: −38 ppm
$J^3$ ($^{19}$F-$^1$H): 46 Hz

EXAMPLE 2

The fluorination of p-toluene-N-neo-pentylsulfonamide was carried out in accordance with Example 1, except in a 1:1 mixture of $CH_2Cl_2$ and $CCl_3F$. After the same reaction time as in Example 1, the supply of fluorine was shut off and the reaction mixture was worked up. 2.4 grams product, 2.1 grams tosylfluoride (byproduct), and 14.0 grams unreacted educt were recovered. Further decomposition products were not isolated. The degree of conversion in this Example thus amounted to 30 percent, and the selectivity was 53.3 percent.

EXAMPLE 3

(a) The fluorination of p-toluene-N-methylsulfonamide (5 g=approx. 27 mmol) took place in a temperature-controlled reactor at −30° C. with a fluorine concentration of 15 volume percent (in N$_2$). A 2:1 mixture of CCl$_3$F and CH$_3$CN was utilized as the solvent. After the reaction mixture was worked up in accordance with Example 1, 4.3 g product (21.2 mmol) were isolated, a 78.5 percent yield. The distillation of the solid material, which melted at 47° C., took place at 90° C. and 3×10$^{-2}$ torr.

$\delta^{19}$F-NMR: −37 ppm $J^3$ ($^{19}$F-$^1$H): 32 Hz

The compounds listed in the following Table were also obtained in a corresponding manner:

| R$^1$ or R$^3$ | R$^2$ | $\delta$ $^{19}$F(ppm)(N—F) | $^3$J ($^{19}$F—$^{19}$F)(Hz) |
|---|---|---|---|
| p-tolyl | n-butyl | −50.3 | 41.0 t |
| p-tolyl | n-propyl | −50.3 | 41.2 t |
| CF$_3$ | CH$_3$ | −40.68 | 6.9 d (F—F) |
|  |  |  | ~30 m (F—H) |
| CF$_3$ | n-butyl | −40.0 | d (F—F) |
|  |  |  | m (F—H) |
| C$_6$F$_5$ | n-propyl | −50.2 | 40.05 t |
| C$_6$F$_5$ | neo-pentyl | −36.6 | 40.05 t |
| tert-butyl | CH$_3$ | −39.76 | 34.33 q |
| tert-butyl | neo-pentyl | −52.7 | 40.05 t |
| tert-butyl | n-butyl | −52.7 | 42.3 t |

Reference Standard: CCl$_3$F
Measurement Frequency: 75.26 megahertz.

The foregoing description has been set forth merely to illustrate the invention and is not intended to be limiting. Since modifications of the described embodiments incorporating the spirit and substance of the invention may occur to persons skilled in the art after a consideration of the foregoing description, the scope of the invention should be limited only with reference to the appended claims and equivalents.

We claim:

1. A process for producing N-fluorosulfonamides comprising reacting a sulfonamide corresponding to the Formula (I):

$$R^1—SO_2—NH—R^2 \qquad (I)$$

in which
R$^1$ represents alkyl with 1 to 10 C-atoms or alkyl with 1 to 10 C-atoms substituted by at least 1 F-atom, or aryl or aryl substituted by 1 to 5 substituents independently selected from the group consisting of F-atoms, CF$_3$-groups, and CH$_3$- groups, with the proviso that not more than 2 substituents may be CF$_3$-groups or CH$_3$-groups, and
R$^2$ represents alkyl containing 1 to 6 C-atoms, with elemental fluorine in a solvent mixture comprising a halogenated hydrocarbon and a nitrile, and recovering the resulting N-fluorosulfonamide from the reaction mixture.

2. A process according to claim 1, wherein R$^1$ represents a perfluoroalkyl group.

3. A process according to claim 2, wherein R$^1$ represents a trifluoromethyl group.

4. A process according to claim 1, wherein R$^1$ represents an aryl group selected from the group consisting of tolyl, trifluoromethylphenyl, fluorophenyl, and perfluorophenyl.

5. A process according to claim 1, wherein said halogenated hydrocarbon is selected from the group consisting of chlorohydrocarbons and fluorochlorohydrocarbons having 1 to 3 C-atoms.

6. A process according to claim 5, wherein said halogenated hydrocarbon is selected from the group consisting of dichloromethane, chloroform, carbon tetrachloride, fluorotrichloromethane, trifluorotrichloroethane, and tetrafluorodichloroethane.

7. A process according to claim 1, wherein said nitrile comprises at least one member selected from the group consisting of acetonitrile and propionitrile.

8. A process according to claim 1, wherein said halogenated hydrocarbon and said nitrile are utilized in a volume ratio from 10:1 to 1:10.

9. A process according to claim 8, wherein said halogenated hydrocarbon and said nitrile are utilized in a volume ratio from 2:1 to 1:2.

10. A process according to claim 1, wherein said fluorine is utilized in admixture with an inert gas, said admixture containing up to 30 volume percent fluorine.

11. A process according to claim 10, wherein said admixture contains from 10 to 25 volume percent fluorine.

12. A process according to claim 1, wherein the reaction mixture is brought into contact with an adsorption agent for hydrogen fluoride during or after the reaction.

13. A continuous process for producing N-fluorosulfonamides according to claim 1, wherein
   (a) a solution of a sulfonamide corresponding to Formula (I) in a solvent mixture of halogenated hydrocarbon and nitrile is continuously introduced into a thermostatically-controlled reactor together with gaseous fluorine to form a reaction mixture,
   (b) the reaction mixture is circulated in a circuit through an adsorption agent for hydrogen fluoride, and
   (c) the reaction mixture is continuously withdrawn from the reactor or the circuit of step (b) in an amount corresponding to the introduction of reaction components.

14. A continuous process according to claim 13, wherein the withdrawn reaction mixture from step (c) is further treated with a hydrogen fluoride adsorption agent to remove any hydrogen fluoride still contained therein.

15. A continuous process according to claim 13, wherein the N-fluorosulfonamide is isolated from the withdrawn reaction mixture by means of a chromatographic process.

16. A continuous process according to claim 13, wherein the N-fluorosulfonamide is isolated from the withdrawn reaction mixture by distillation.

* * * * *